United States Patent
Conley et al.

(10) Patent No.: US 9,883,859 B2
(45) Date of Patent: Feb. 6, 2018

(54) FLEXIBLE SUTURE ANCHOR THREADER AND SUTURE ANCHOR KIT

(71) Applicant: DePuy Synthes Products, Inc., Raynham, MA (US)

(72) Inventors: Jordan P. Conley, West Chester, PA (US); Scott P. Larsen, West Chester, PA (US); James Hearn, Wester Chester, PA (US); Patrick Swindon, Cincinnati, OH (US)

(73) Assignee: DePuy Synthes Products, Inc., Raynham, MA (US)

( * ) Notice: Subject to any disclaimer, the term of this patent is extended or adjusted under 35 U.S.C. 154(b) by 82 days.

(21) Appl. No.: 14/694,000

(22) Filed: Apr. 23, 2015

(65) Prior Publication Data

US 2015/0305737 A1    Oct. 29, 2015

Related U.S. Application Data

(60) Provisional application No. 61/984,281, filed on Apr. 25, 2014.

(51) Int. Cl.
*A61B 17/04* (2006.01)
*A61B 17/00* (2006.01)

(52) U.S. Cl.
CPC ...... *A61B 17/0485* (2013.01); *A61B 17/0401* (2013.01); *A61B 2017/00862* (2013.01); *A61B 2017/00867* (2013.01); *A61B 2017/0403* (2013.01); *A61B 2017/044* (2013.01); *A61B 2017/0414* (2013.01)

(58) Field of Classification Search
CPC ............ A61B 17/0485; A61B 17/0401; A61B 17/0469; A61B 2017/00349; A61B 2017/0409; D05B 7/00

USPC .................... 223/99; 606/139, 144, 148, 232
See application file for complete search history.

(56) References Cited

U.S. PATENT DOCUMENTS

| | | | |
|---|---|---|---|
| 2,042,403 A * | 5/1936 | Hrivnak | D05B 87/00 223/99 |
| 2,167,080 A * | 7/1939 | Mason | D05B 87/00 223/99 |
| 2,416,260 A | 2/1947 | Karle | |
| 5,251,797 A | 10/1993 | Martin | |
| 5,501,692 A | 3/1996 | Riza | |

(Continued)

FOREIGN PATENT DOCUMENTS

EP    2 676 612    12/2013

OTHER PUBLICATIONS

International Search Report and Written Opinion (PCT/US2015/027230); dated Jul. 14, 2015.

*Primary Examiner* — Katherine M Shi
(74) *Attorney, Agent, or Firm* — Dunlap Codding, P.C.

(57) ABSTRACT

A suture anchor kit includes an anchor body having a central bore extending from an opening at a proximal end of the anchor body through a portion of the length thereof. A transverse member is disposed in the central bore such that the ends of the transverse member extend across the bore to the anchor body. A suture anchor threading apparatus may have a handle and a suture threader extending from the handle. The suture threader has a wire loop open sufficiently to accept at least one suture and is made of an elastic material having a resiliency sufficient to bend 120° to 180° about a 1 mm to 4 mm radius without permanent deformation.

10 Claims, 2 Drawing Sheets

(56) References Cited

U.S. PATENT DOCUMENTS

| | | |
|---|---|---|
| 5,800,447 A | 9/1998 | Wenstrom, Jr. |
| 5,899,920 A | 5/1999 | DeSatnick et al. |
| 5,906,624 A | 5/1999 | Wenstrom, Jr. |
| 6,022,360 A | 2/2000 | Reimels et al. |
| 8,118,835 B2 | 2/2012 | Weisel et al. |
| 2005/0222618 A1 | 10/2005 | Dreyfuss et al. |
| 2006/0106423 A1* | 5/2006 | Weisel ............... A61B 17/0401 606/232 |
| 2008/0275476 A1 | 11/2008 | Cropper et al. |
| 2009/0088798 A1 | 4/2009 | Snyder et al. |
| 2010/0063542 A1* | 3/2010 | van der Burg ..... A61B 17/0401 606/232 |
| 2013/0035699 A1* | 2/2013 | Heneveld ........... A61B 17/0057 606/144 |
| 2013/0079819 A1 | 3/2013 | Rohlinger et al. |
| 2013/0144336 A1* | 6/2013 | Snyder ............... A61B 17/0401 606/232 |
| 2013/0345749 A1* | 12/2013 | Sullivan ............ A61B 17/0401 606/232 |

* cited by examiner

FLEXIBLE SUTURE ANCHOR THREADER AND SUTURE ANCHOR KIT

CROSS REFERENCE TO RELATED APPLICATION

This application claims priority to U.S. Provisional Application Ser. No. 61/984,281 filed on Apr. 25, 2014, the entire content of which is hereby expressly incorporated herein by reference.

BACKGROUND OF THE INVENTIVE CONCEPTS

In many situations, soft tissue may need to be attached (or re-attached) to bone. As an example, a ligament or tendon may have been detached from bone as the result of injury, and appropriate repair may require re-attaching the ligament or tendon to its host bone. The use of sutures together with one or more suture anchors is one way of attaching soft tissue to bone. Suture anchors generally include a body that is deployed in bone with one or more sutures extending from the body. The sutures may then be used to secure the soft tissue to the bone, e.g., by passing the sutures through the tissue and then knotting the suture so as to hold the tissue in position relative to the bone.

Certain prior art suture anchors have eyelets extending from the proximal end that require countersinking of the eyelet below the bone surface to avoid having the patient's tissue abrade against the exposed eyelet. However, this countersinking can make the suture attached to the eyelet vulnerable to abrasion. To avoid countersinking and abrasion, threaded suture anchors have been developed which have a transverse anchor pin disposed inside the body of the suture anchor. The pin provides a support over which a suture can be looped and secured in a recessed fashion within the anchor.

Many such suture anchors are configured such that the sutures need to be attached to the suture anchor either at the time of manufacture or in the operating room prior to use. In either case, the sutures are attached to the body of the suture anchor prior to deployment of the suture anchor in the body. As a result, a surgeon may be constrained by the configuration of the suture anchor once it has been deployed in the body. In other words, with many suture anchor constructions, the number and types of sutures selected by the surgeon prior to deployment in the bone significantly constrains the choices available to the surgeon after the suture anchor has been deployed in the bone. This can be a significant limitation since, in many circumstances, the surgeon may wish to adjust a procedure in response to tissue conditions, which may only become apparent after the procedure has commenced.

One suture anchor that permits sutures to be loaded into the suture anchor after the suture anchor has been deployed in the bone is disclosed in U.S. Publication No. 2009/0088798 by Snyder et al. The suture anchor utilizes a flexible pin or crossbar extending across an axial recess of the anchor such that when a distally directed force is applied to the crossbar, a suture may be passed by the crossbar, and when a proximally directed force is applied to the suture, the crossbar is captured, thereby capturing the suture.

It would be advantageous if a suture anchor having a recessed, rigid pin or crossbar could be threaded with one or more sutures after the suture anchor has been deployed in the bone. The inventive concepts disclosed herein are directed to such a suture threader and suture anchor assembly.

DETAILED DESCRIPTION OF EXEMPLARY EMBODIMENTS

Figure 1:
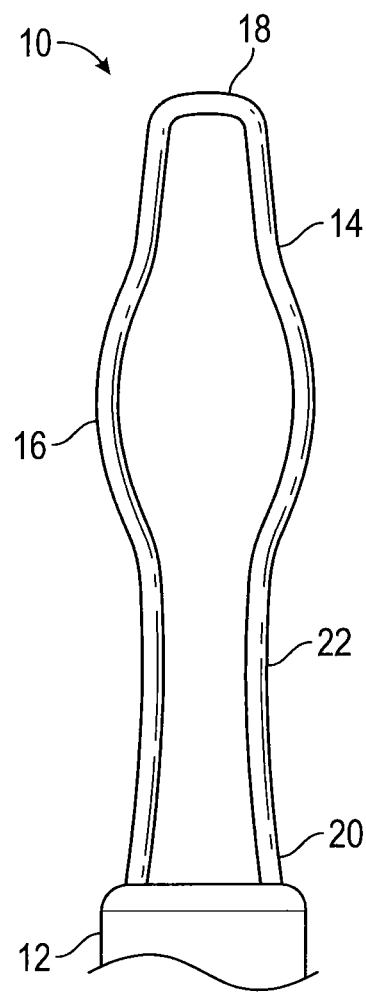
FIG. 1 is a plan view of a suture anchor threading apparatus constructed in accordance with the inventive concepts disclosed herein.

Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for the purpose of description only and should not be regarded as limiting in any way.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Figure 2:
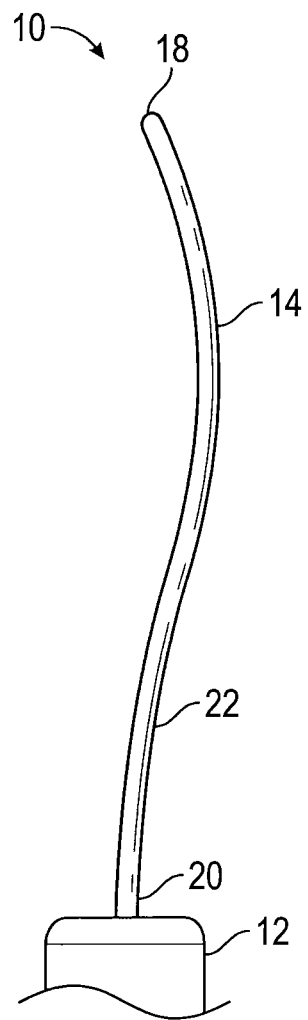
FIG. 2 is a side elevational view of the suture anchor threading apparatus of FIG. 1.

Referring to the drawings, and more particularly to FIGS. 1 and 2, a suture anchor threading apparatus 10 constructed in accordance with the inventive concepts disclosed herein is illustrated. The suture anchor threading apparatus 10 includes a handle 12 and a suture threader 14 extending from the handle 12. The suture threader 14 includes a wire loop 16 sufficiently open to accept one or more sutures. At least a distal portion 18 of the suture threader 14 has a longitudinal profile curvature to aid in bending the suture threader 14 about a curve when forced against a flat or curved surface. In one embodiment, as best shown in FIG. 2, most of the wire loop 16 has a longitudinal profile curvature.

The handle 12 facilitates a surgeon in inserting and positioning the suture threader 14 during surgery. The handle 12 may be connected to a proximal end 20 of the suture threader 14. The handle 12 can be made of materials including, but not limited to, titanium, titanium alloys, stainless steel, ceramics, and/or polymers. Handle materials that cannot be autoclaved and/or chemically sterilized may be made of sterile materials.

Conventional needle threaders and conventional suture anchor threaders are designed to compress and narrow a wire loop portion in order to pass through a straight transverse bore, such as a needle eye or a transverse bore in a suture anchor. The wire loop re-expands upon exit from the eye or bore in order to provide a large target area for passing a thread. The presently disclosed and claimed suture threader 14 is also configured to narrow upon insertion into a smaller diameter bore. However, while conventional threaders work only with straight bores, the presently disclosed suture anchor threading apparatus 10 is much more versatile and can resiliently bend about structures, as necessary.

The wire loop 16 of the suture anchor threading apparatus 10 is made of an elastic material having a resiliency sufficient to bend 120° to 180° about a 1 mm to 4 mm radius without permanent deformation. In one embodiment, the elastic material comprises a superelastic alloy.

Superelasticity or pseudoelasticity is an elastic or reversible response to applied stress caused by a phase transformation. For example, it can be caused by a phase transformation between austenitic and martensitic phases of a crystal. When mechanically loaded, a superelastic material deforms reversibly to very high strains by the creation of a stress-induced phase. When the load is removed, the new phase becomes unstable and the material regains its original shape. Unlike shape-memory alloys, no change in temperature is needed for the alloy to recover its initial shape. Examples of a superelastic alloy include nitinol, a nickel and titanium alloy.

Non-limiting examples of suitable superelastic alloys are nitinol, a nickel-titanium alloy having a mol ratio of nickel to titanium of about 1:1, and Triton™ alloy, another form of nitinol having superelastic properties but a higher bending modulus. It is anticipated that additional elastic materials including alloys and composites will be developed that have a resiliency sufficient to bend 120° to 180° about a 1 mm to 4 mm radius without permanent deformation.

In one embodiment, the suture threader 14 includes a neck 22 interconnecting the wire loop 16 and the handle 12 to provide additional reach. The neck 22 can be formed of the same or different material as the wire loop 16. In one embodiment, the neck 22 and the wire loop 16 are formed of a single wire. In another embodiment, the single wire comprises nitinol.

Figure 3:
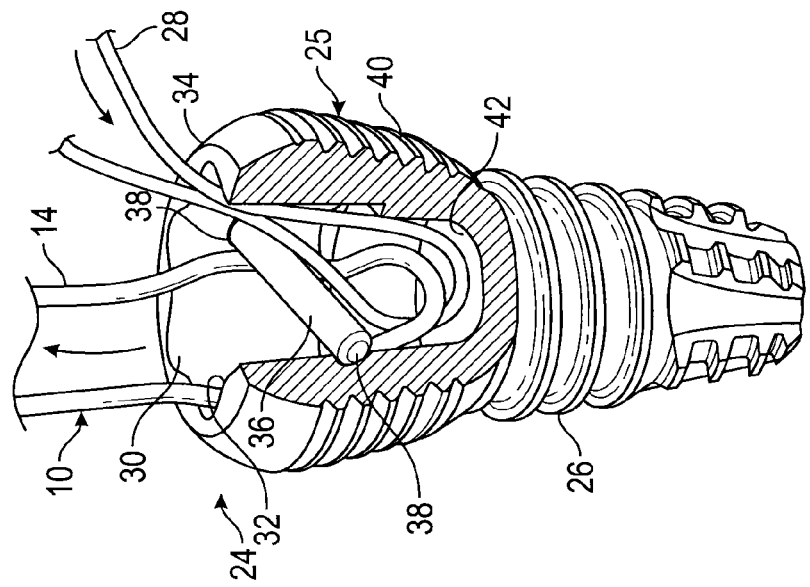
FIG. 3 is a perspective view of a suture anchor kit constructed in accordance with the inventive concepts disclosed herein.
Figure 4:
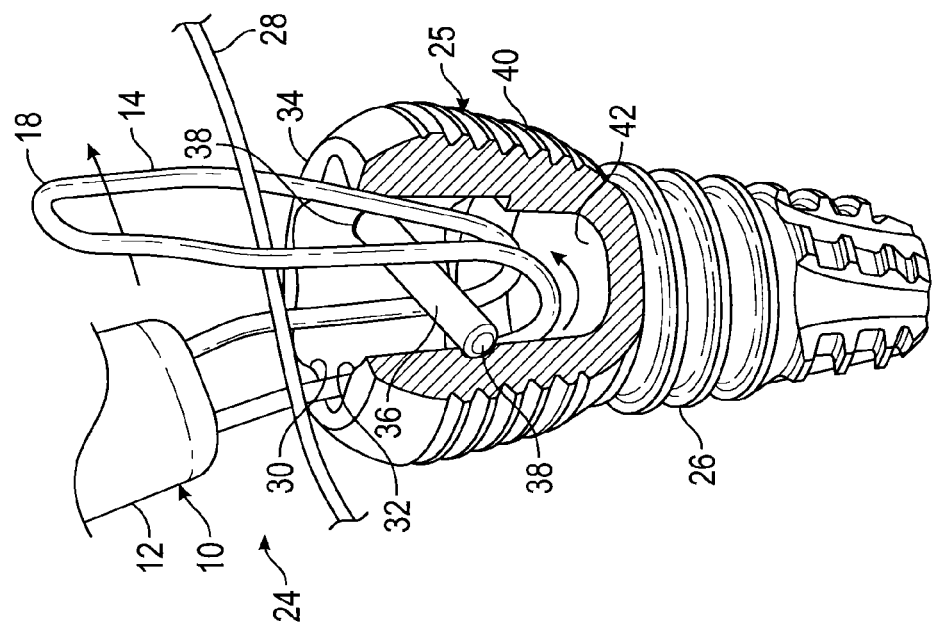
FIG. 4 is a perspective view of the suture anchor kit of FIG. 3 showing a suture being looped about a transverse member of a suture anchor.

Referring now to FIGS. 3 and 4, a suture anchor kit 24 constructed in accordance with the inventive concepts disclosed herein is illustrated. The suture anchor kit 24 includes the suture anchor threading apparatus 10 described above, and a suture anchor 25 having an anchor body 26 to which one or more sutures 28 can be attached. In one embodiment, the anchor body 26 has a central bore 30 extending from an opening 32 at a proximal end 34 of the anchor body 26. A transverse member 36 is disposed in the central bore 30 having ends 38 that attach to a sidewall 40 of the central bore 30, providing a "pin" about which the one or more sutures 28 can be looped.

Upon insertion of the suture threader 14 into the central bore 30, the curved distal portion 18 of the suture threader 14 eventually meets and is deflected by a distal surface 42. In one embodiment, the distal surface 42 is curved to assist in deflecting the suture threader 14. Without a curvature present in at least one of the distal portion 18 of the suture threader 14 and the distal surface 42 of the central bore 30, the suture threader 14 could crimp in use rather than resiliently bend 120° to 180° behind the transverse member 36. The bend must be made within the confines of the central bore 30 which typically has a radius in the range of about 1 mm to 4 mm.

In one embodiment, the transverse member 36 is also formed of a superelastic material such as nitinol.

In another embodiment, the suture anchor kit 24 includes at least one suture 28.

The suture anchor 25 as described above can be threaded by inserting the wire loop 16 of the suture threader 14 through the opening 32 of the anchor body central bore 30 on a first side of the transverse member 36. The wire loop 16 is manipulated around the transverse member 36 and back out the opening 32 on a second side of the transverse member 36. The wire loop 16 is made of an elastic material as described above and having a resiliency sufficient to bend 120° to 180° about a 1 mm to 4 mm radius without permanent deformation. At least a distal portion 18 of the wire loop 16 has a longitudinal profile curvature to aid in making the curved path about the transverse member 36. One or more sutures 28 are inserted through the wire loop 16 of the suture threader 14 on the second side of the transverse member 36. The wire loop 16 is then retracted from the central bore 30 such that the one or more sutures 28 are looped around the transverse member 36 with suture ends (not shown) extending through the opening 32.

In some cases, it may be advantageous to thread the suture threader 14 before pulling through the anchor body 26. In such situations, the suture anchor 25 as described above can be threaded by first inserting one or more sutures 28 through the wire loop 16 of the suture threader 14. The wire loop 16 with the one or more sutures 28 is manipulated through the opening 32 of the central bore 30 on a first side of the transverse member 36, around the transverse member 36, and back out the opening 32 on a second side of the transverse member 36. The wire loop 16 is then retracted from the central bore 30 while securing the threaded portion on the second side of the transverse member 36 such that the one or more sutures 28 are looped around the transverse member 36 with suture ends (not shown) extending through the opening 32.

The suture anchor threading apparatus 10 can be used to thread the suture anchor 25 either before or after the suture anchor 25 is inserted into a patient's body. In one embodiment, the suture anchor 25 is first inserted into and secured in the patient before it is threaded with a suture.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or defined in the appended claims.

What is claimed is:

1. A suture anchor kit, comprising:
   an anchor body having a central bore extending from an opening at a proximal end of the anchor body through a portion of the length thereof, and a transverse member disposed in the central bore and having ends that extend across the bore and attach to the anchor body; and a suture anchor threading apparatus comprising a rigid handle and a suture threader extending from the rigid handle, the suture threader having a wire loop forming an opening and having a proximal end connected to the handle, a closed distal end, a closed first side extending from the proximal end to the closed distal end, a closed second side extending from the proximal end to the closed distal end and opposite the closed first side, an open front end, and an open rear end, the opening extending from the open front end to the open rear end and being open sufficiently to accept at least one suture, the wire loop comprising an elastic material having a resiliency sufficient to bend 120° to 180° about a 1 mm to 4 mm radius without permanent deformation, at least a distal portion of the wire loop having a longitudinal side profile curvature, wherein the central bore of the anchor body is contoured to deflect the wire loop around the transverse member upon inserting the wire loop into the central bore on a first side of the transverse member contacting a distal end of the central bore so as to cause the wire loop to bend around the transverse member and extend from the central bore on a second side of the transverse member.

2. The suture anchor kit of claim 1, wherein the wire loop is configured to narrow upon insertion into the anchor body bore, curve about the transverse member, and resume its original shape upon exit of the anchor body bore to receive the at least one suture therethrough.

3. The suture anchor kit of claim 1, wherein the bore is thimble shaped with a rounded distal surface.

4. The suture anchor kit of claim 1, wherein the elastic material comprises a superelastic alloy.

5. The suture anchor kit of claim 1, wherein the elastic material comprises an alloy of nickel and titanium.

6. The suture anchor kit of claim 1, wherein the elastic material comprises nitinol.

7. The suture anchor kit of claim 1, further comprising a neck, the neck interconnecting the wire loop and the rigid handle.

8. The suture anchor kit of claim 7, wherein the neck and wire loop are formed of a single wire.

9. The suture anchor kit of claim 8, wherein the single wire comprises nitinol.

10. The suture anchor kit of claim 1, wherein the transverse member comprises nitinol.

* * * * *